(12) United States Patent
Zabudkin et al.

(10) Patent No.: US 7,053,191 B2
(45) Date of Patent: May 30, 2006

(54) METHOD OF PREPARING 4-R-SUBSTITUTED 4-DEMETHOXYDAUNORUBICIN

(75) Inventors: Alexander F. Zabudkin, Donetsk (UA); Victor Matvienko, Donetsk (UA); Alexey Matvyeyev, Donetsk (UA); Aleksandr M. Itkin, San Diego, CA (US)

(73) Assignee: Solux Corporation, San Diego, CA (US)

( * ) Notice: Subject to any disclaimer, the term of this patent is extended or adjusted under 35 U.S.C. 154(b) by 0 days.

(21) Appl. No.: 10/831,448

(22) Filed: Apr. 23, 2004

(65) Prior Publication Data

US 2004/0236086 A1 Nov. 25, 2004

Related U.S. Application Data

(60) Provisional application No. 60/472,192, filed on May 21, 2003.

(51) Int. Cl.
C07H 15/24 (2006.01)

(52) U.S. Cl. ...................................... 536/6.4
(58) Field of Classification Search ................ 536/6.4
See application file for complete search history.

(56) References Cited

U.S. PATENT DOCUMENTS

| | | |
|---|---|---|
| 3,963,760 A | 6/1976 | Bernardi et al. |
| 4,012,284 A | 3/1977 | Di Marco et al. |
| 4,154,745 A | 5/1979 | Kende et al. |
| 4,161,480 A | 7/1979 | Pappo et al. |
| 4,298,535 A | 11/1981 | Vogel et al. |
| 4,448,724 A | 5/1984 | Cava et al. |
| 4,471,052 A | 9/1984 | Mitscher et al. |
| 4,489,206 A | 12/1984 | Cava et al. |
| 4,496,485 A | 1/1985 | Garland |
| 4,564,674 A | 1/1986 | Terashima et al. |
| 4,697,005 A | 9/1987 | Swenton et al. |
| 4,973,674 A | 11/1990 | Brasca et al. |
| 4,985,548 A | 1/1991 | Caruso et al. |
| 5,130,029 A | 7/1992 | Suutarinen |
| 5,162,512 A | 11/1992 | King et al. |
| 5,180,758 A | 1/1993 | Cabri et al. |
| 5,218,130 A | 6/1993 | Cabri et al. |
| 5,510,469 A | 4/1996 | Faiardi et al. |
| 5,587,495 A * | 12/1996 | Cabri et al. ............... 552/220 |
| 5,731,313 A | 3/1998 | Suarato et al. |
| 5,776,458 A | 7/1998 | Angelucci et al. |
| 5,874,412 A | 2/1999 | Priebe et al. |
| 5,945,518 A | 8/1999 | Bigattie et al. |
| 5,985,887 A | 11/1999 | Caruso et al. |
| 5,998,615 A | 12/1999 | Suarato et al. |
| 6,096,888 A | 8/2000 | Suarato et al. |
| 6,194,422 B1 | 2/2001 | Caruso et al. |
| 6,218,519 B1 | 4/2001 | Kenten et al. |
| 6,512,101 B1 | 1/2003 | King et al. |

FOREIGN PATENT DOCUMENTS

| | | |
|---|---|---|
| EP | 0328399 A2 | 8/1989 |
| EP | 0335369 A2 | 10/1989 |
| EP | 0436474 A1 | 7/1991 |
| WO | WO 01/25179 A1 | 4/2001 |
| WO | WO 01/87814 A2 | 11/2001 |

* cited by examiner

*Primary Examiner*—Shaojia A. Jiang
*Assistant Examiner*—Ganapathy Krishnan
(74) *Attorney, Agent, or Firm*—Vista IP Law Group LLP

(57) ABSTRACT

A method of synthesizing 4-R-substituted anthracyclines and their corresponding salts from 4-demethyldaunorubicin includes the steps of treating 4-demethyldaunorubicin with a sulfonylating agent to form 4-demethyl-4-sulfonyl-$R_3$-daunorubicin. 4-Demethyl-4-$R_3$-sulfonyl-daunorubicin is then subject to a reducing agent in the presence of a transition metal catalyst in a temperature range of about 30° C. to about 100° C. in a polar aprotic solvent in an inert atmosphere. Protected 4-demethoxy-4-R-daunomycin then undergoes hydrolysis in a basic solution to form the 4-R-substituted anthracyclines. The novel method lacks the step of forming a stereospecific glycoside bond between aglycone and aminoglycoside. The method also increases the yield of the final product up to 30 to 40%.

13 Claims, No Drawings

METHOD OF PREPARING 4-R-SUBSTITUTED 4-DEMETHOXYDAUNORUBICIN

RELATED APPLICATIONS

This Application claims priority to U.S. provisional Application No. 60/472,192 filed on May 21, 2003. U.S. provisional Application No. 60/472,192 is incorporated by reference as if set forth fully herein.

FIELD OF THE INVENTION

The field of the invention generally relates to chemical methods used to produce anthracyclines. More specifically, the field of the invention relates to methods and processes used to produce 4-R-substituted 4-demethoxydaunorubicin having the formula (I) described more fully herein from 4-demethyldaunorubicin. In the case where R=H, the present invention relates to chemical methods and processes used to produce idarubicin from 4-demethyldaunorubicin.

BACKGROUND OF THE INVENTION

Anthracyclines form one of the largest families of naturally occurring bioactive compounds. Several members of this family have shown to be clinically effective anti-neoplastic agents. These include, for example, daunorubicin, doxorubicin, idarubicin, epirubicin, pirarubicin, zorubicin, aclarubicin, and carminomycin. For instance, these compounds have shown to be useful in bone marrow transplants, stem cell transplantation, treatment of breast carcinoma, acute lymphocytic and non-lymphocytic leukemia, chronic lymphocytic leukemia, non-Hodgkin's lymphoma, and other solid cancerous tumors.

Currently known methods used to prepare 4-demethoxy-4-R-daunorubicin-type anthracyclines (where R=H the anthracycline is known as idarubicin) are based on coupling of the aglycone (synthesized by any of the known methods) and protected and activated daunosamine in the presence of silver triflate ($AgOSO_2CF_3$), trimethylsilyltriflate ($(CH_3)_3SiOSO_2CF_3$), or a mercuric oxide—mercuric bromide system ($HgO$—$HgBr_2$). For example, it is currently known to synthesize aglycone using either anthracenetetrone or isobenzofurane as the starting substance. Unfortunately, these methods of aglycone synthesis are complicated by the creation of optically active centers at carbons C7 and C9.

An alternative method of synthesis of 4-demethoxy-daunorubicin (idarubicin) utilizes daunorubicin aglycone which is prepared by the acidic hydrolysis of daunorubicin starting material. In this method, at the same time daunosamine is synthesized, with chemical modification, the daunosamine can be further used for glycosylation of the modified aglycone. Earlier methods involved the substitution of 4-MeO aglycone substituent for hydrogen, $NH_2$, or other chemical groups involved demethylation of daunorubicinone, sulfonation of the resulting 4-demethoxydaunorubicinone and substitution of the 4-$ArSO_2O$ radical for a 4-$ArCH_2NH$ with further reduction of the benzyl radical leading to formation of 4-$NH_2^-$ radical. See U.S. Pat. No. 4,085,548 entitled 4-DEMETHOXY-4-AMINO-ANTHRACYCLINES, issued Jan. 15, 1991, to Caruso et al., the disclosure of which is incorporated by reference as if set forth fully herein. Further reductive deamination results in production of 4-demethoxydaunorubicin (idarubicin). See EP Application No. 0328399, published Aug. 16, 1989, the disclosure of which is incorporated by reference as if set forth fully herein.

There also has been described a reductive cross-condensation reaction of 4-demethyl-4-Tf-daunorubicinone on the phosphorous hydride—$Pd^0$ catalyzing complexes. See U.S. Pat. No. 5,587,495. In these reactions, 4-R substituted daunorubicinones are produced wherein R=

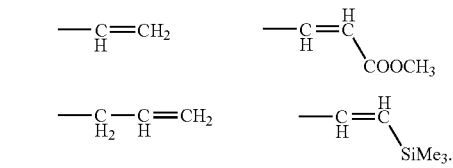

Similarly, reductive carbonylation of 4-Tf-daunorubicinone on the same catalysts described above results in 4-COOR substituted daunorubicinones. See U.S. Pat. No. 5,218,130. When formate is utilized as a ligand, substitution of 4-O-Tf radical for hydrogen takes place resulting in formation of 4-demethoxydaunorubicinone. See U.S. Pat. No. 5,103,029.

SUMMARY OF THE INVENTION

The present invention relates to processes used to prepare 4-R-substituted anthracyclines and their corresponding salts of formula (I) shown below from 4-demethyldaunorubicin:

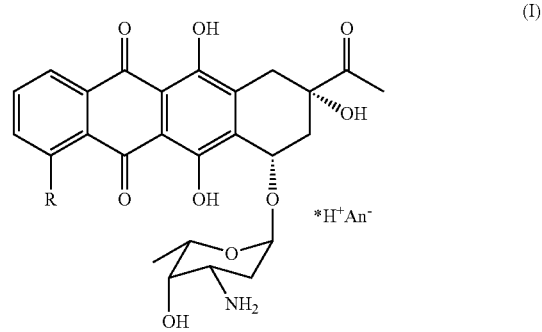

Wherein R is defined as hydrogen, a linear or branched oxy[alkyl, alkenyl or alkynyl] group comprised of one to sixteen carbon atoms, or a complex ester group $COOR_1'$, wherein $R_1'$ is a linear or branched alkyl, alkenyl or alkyne group of up to ten carbon atoms, comprising the steps of:

(1) providing 4-demethyldaunorubicin or a derivative of 4-demethyldaunorubicin of formula (II)

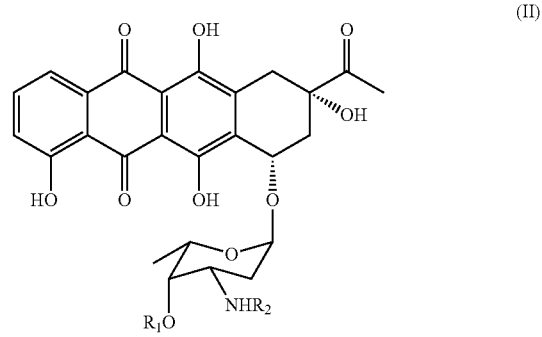

wherein $R_1$ comprises H, acyl or acyl halide and $R_2$ comprises H, acyl or acyl halide, carbonate, or Schiff's base (2) treating the 4-demethyldaunorubicin or the derivative of 4-demethyldaunorubicin of formula (II) with a sulfonylating agent having a chemical formula $R_3$—$SO_2$—X, wherein $R_3$ is an alkyl group, an alkyl halide group or an aryl group, X is a halide group or —O—$SO_2$—$R_3$ to form 4-demethyl-4-sulfonyl-daunorubicin having formula (III)

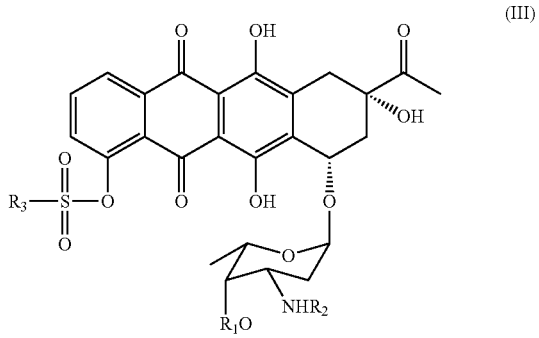

(III)

wherein $R_3$ comprises an alkyl group having from 1 to 4 carbon atoms optionally substituted by one or more halogen atoms or an aryl group optionally substituted by halogen, alkyl, aloxy or nitro, $R_1$ comprises hydrogen, acyl, or acyl halide, and $R_2$ comprises hydrogen, acyl, acyl halide, carbonate, or Schiff's base;

(3) reacting the 4-demethyl-4-sulfonyl-daunorubicin of formula (III) with a reducing agent in the presence of catalytic quantities of a compound having formula (IV)

$$ML_pL'_q \qquad (IV)$$

wherein M represent a transition metal atom; L and L', wherein L and L' represent the same or different anions or a neutral molecule, and p and q may vary from zero to four, to produce protected 4-demethoxydaunomycin having a formula (V),

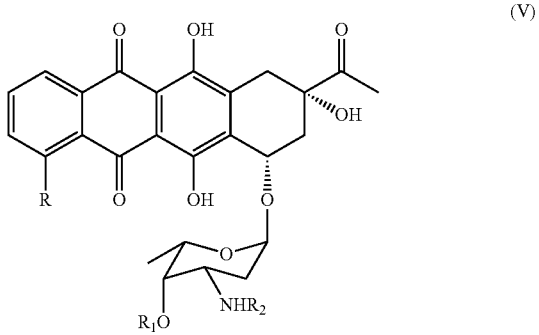

(V)

(4) hydrolyzing the protected 4-demethoxydaunomycin in a basic solution to produce a 4-R-substituted anthracycline of formula (I).

The present invention uses a novel method of synthesis which lacks the step of forming a stereospecific glycoside bond between aglycone and aminoglycoside. The inventors have found that the novel method of synthesis increases the yield of the final product to up to 30–40% from (II). It thus is an object of the invention to provide a method of synthesis which reduces the number of steps involved to produce 4-R-substituted 4-demethoxydaunorubicin. It is a further object of the invention to provide a method of synthesis which increases the yield of the process.

DETAILED DESCRIPTION OF THE INVENTION

The present invention is directed to methods used to prepare 4-R-substituted anthracyclines and their corresponding salts of formula (I) shown below

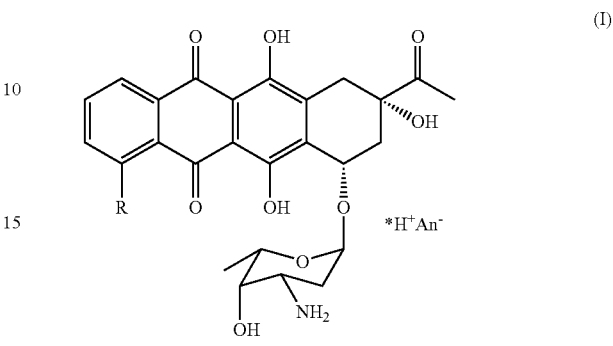

(I)

Formula (I) illustrates a salt of a 4-R-substituted anthracyclines. It should be understood, however, that the present method contemplates the synthesis of 4-R-substituted anthracyclines of formula (I) in both the salt and non-salt forms. With respect to the salt form shown in Formula (I), $An^-$ is preferably a anion of a strong acid, for example, hydrochloric or hydrobromic acid. In Formula (I), R may comprise hydrogen (for example, in the case of idarubicin), a linear or branched oxy[alkyl, alkenyl, or alkynyl] group comprised of between one to sixteen carbon atoms. In the case of a linear or branched oxy[alkyl, alkenyl, or alkynyl] group, R preferably has less than or equal to four carbon atoms.

The linear or branched oxy[alkyl, alkenyl, or alkynyl] group may be partially substituted for an aryl group (both unsubstituted and substituted) for any inert group such as, for example, an alkyl group, an alkoxy group, or a nitro group. In addition, the linear or branched oxy group may be partially substituted for an alkoxy group, a trialkylsilyl group, ester group, or amide group.

R may also comprise a complex ester group, $COOR_1'$, where $R_1'$ is a linear or branched alkyl, alkenyl or alkyne group of up to ten carbon atoms.

The synthesis of the 4-R-substituted anthracycline of formula (I) begins by providing a starting compound, preferably 4-demethyldaunorubicin or a derivative of 4-demethyldaunorubicin of formula (II)

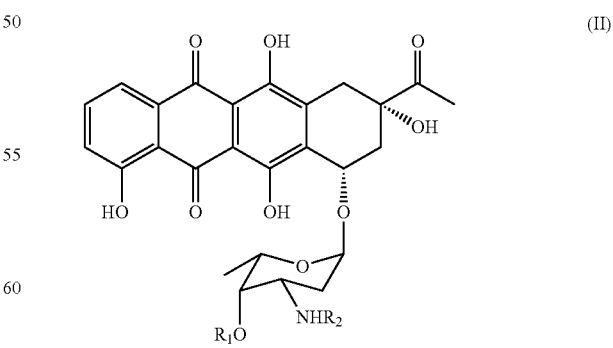

(II)

wherein $R_1$ comprises H, acyl or acyl halide and $R_2$ comprises H, acyl or acyl halide, carbonate, or Schiff's base; (preferably $COCF_3$).

Next, the compound of formula (II) is treated with a sufonylating agent having the chemical formula R₃—SO₂—X, where R₃ comprises an alkyl group, alkyl halide group or an aryl group and X comprises a halide or —O—SO₂—R₃. The reaction is preferably conducted in pyridine in the presence of sterically hindered tertiary amine, for example, N, N-diisoprolylethylamine, and catalytic quantities of N, N-dimethylaminopyridine. The reaction involves mostly C4-OH. In addition, hydroxyl groups at C6, C11 and C9 react principally in special conditions allowing utilization of unprotected derivatives of the 4-demethyldaunorubicin at these carbon positions. The above steps produce 4-demethyl-4-sulfonyl-daunorubicin having formula (III)

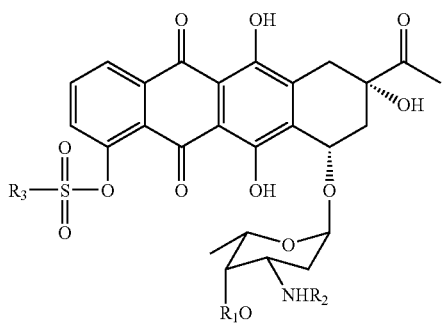

wherein $R_3$ comprises an alkyl group having one to four carbon atoms optionally substituted by one or more halogen atoms or an aryl group optionally substituted by a halogen group, alkyl group, aloxy group, or nitro group. Preferred groups for $R_3$ include trifluoromethyl, 4-fluorophenyl, and 4-tolyl. $R_1$ preferably comprises hydrogen, acyl, or acyl halide. $R_2$ preferably comprises hydrogen, acyl, acyl halide, carbonate, or Schiff's base (i.e., a compound formed by a condensation reaction between an aromatic amine and an aldehyde or ketone).

The 4-demethyl-4-sulfonyl-daunorubicin of formula (III) us then reacted with a reducing agent in the presence of catalytic quantities ($10^4$:1 to 1:1 and preferably 20:1 to 100:1 (in a molar ratio) of a compound having formula (IV) to produce protected 4-demethoxydaunomycin having a formula (V).

$$ML_pL'_q \quad (IV)$$

wherein M represent a transition metal atom, preferably palladium or nickel. L and L', which are the same or different molecules, represent the same or different anions or a neutral molecule. Anions for L and L' include anions such as $HCOO^-$, $CH_3COO^-$, $Cl^-$. Examples of a neutral molecule include neutral solvent molecules, mono or di-phosphine, phosphate or diamine, and preferably a chelating diphosphine such as 1,3-diphenylphosphinopropane, 1,1'-bis(diphenylphosphino)ferrocene, and 1,2-bis[N-(1-phenylethyl),N-(diphenylphosphino)amino]ethane. In formula (IV), p and q may vary from zero to four.

Preferably, the reducing agent is a formiate anion (e.g., formic acids or salts of formic acid) or unsaturated compound such as CO or substituted alkenyl and alkynyl groups in a reducing environment.

Preferably, the reaction is conducted at temperatures in the range from about 30° C. to about 100° C. in a polar aprotic solvent, preferably in alkylamides in an inert atmosphere. Protected 4-demethoxydaunomycin having a formula (V) is shown below.

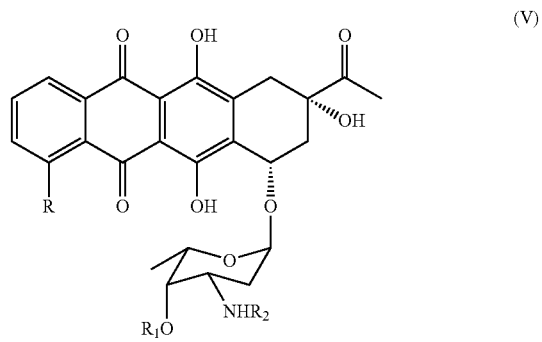

The protected 4-demethoxydaunomycin ($R_1$ or $R_2 \neq H$) is then hydrolyzed to remove the protecting group in a basic solution to produce 4-R-substituted anthracycline of formula (I). Preferably the basic solution is formed in water or alcohol, preferably water or methanol.

The following examples set forth below illustrate a preferred method of preparing a 4-R-substituted anthracycline (idarubicin) of formula (I) from 4-demethyldaunorubicin.

EXAMPLE 1 a) First, 2 g of 3'-trifluoroacetamido-4-demethyldaunorubicin ($R_1$=H, $R_2$=trifluoroacetyl) are dissolved in 0.2 L of pyridine.

b) Next, 4 ml of diisopropylethylamine and 0.5 g of 4-dimethylaminopyridine are added to the solution of step (a) of Example 1.

c) Next, the solution in step (b) of Example 1 is chilled to 0° C. and 2.5 ml of freshly distilled trifluoromethanesulfonic anhydride is added.

d) Next, the solution in step (c) of Example 1 is incubated for 1 hour at room temperature.

e) After incubation, 0.15 L of concentrated hydrochloric acid, 0.2 kg of ice, and 0.2 L of dichloromethane is added to the incubated solution.

f) Next, the organic layer is washed in 0.2 L of distilled water and dichloromethane is removed by evaporation at partial vacuum pressure.

g) After evaporation, 1.5 g of 4-trifluoromethanesulfonyl-3'-trifluoroacetamido-4-demethyldaunorubicin is produced with a purity 85% (Confirmed by HPLC).

h) The 4-trifluoromethanesulfonyl-3'-trifluoroacetamido-4-demethyldaunorubicin from step (g) of Example 1 is used in the next synthetic step in Example 2 with or without additional purification.

EXAMPLE 2 a) 1.5 g of 4-trifluoromethanesulfonyl-3'-trifluoroacetamido-4-demethyldaunorubicin ($R_1$=H, $R_2$=trifluoroacetyl, $R_3$=trifluoromethyl), yielded from synthesis in Example 1, is dissolved in 0.1 L of dimethylformamide.

b) While stirring, 2 g of triethylamine formate and 50 mg of palladium acetate are added to the mixture of step (a) in Example 2 and an argon stream is passed through the mixture.

c) The mixture of step (b) of Example 2 is then heated to 50° C. and 200 mg of 1,1'-bis(diphenylphosphino) ferrocene is added.

d) The mixture of step (c) of Example 2 is heated at 50° C. for 8 hours.

e) The mixture of step (d) of Example 2 is then poured into water with intense stirring with resulting sediment formation (4-demethoxy-3'-trifluoroacetamidodaunomycin).

f) The sediment (4-demethoxy-3'-trifluoroacetamidodaunomycin) is filtered, and then purified by preparative chromatography.

g) The yield of this process is 0.8–0.85 g of 4-demethoxy-3'-trifluoroacetamidodaunomycin of 98% purity (Confirmed by HPLC).

EXAMPLE 3 a) 0.85 g of 4-demethoxy-3'-trifluoroacetamidodaunomycin are added to the stirred water solution of 0.1 N NaOH (0.06 L) and incubated at 30° C. for 30 minutes. The color of the solution turns deep blue-violet.

b) The reactive mixture is then poured with intense stirring into 0.5 L of 10–12% chloroform-in-butanol solution heated to 40° C.

c) Next, while intensely stirring, hydrochloric acid (1:3) is added to the mixture to titrate to a pH of 8.8–9.0.

d) The resulting organic layer is then washed in distilled water.

e) 0.1 L of distilled water is then added to washed organic layer in step (d) of Example 3, and 0.8 N hydrochloric acid is added (0.1 L) to titrate to a pH of 3.5.

f) The solution in step (e) in Example 3 is intensely stirred, and the water layer containing 4-demethoxydaunomycin hydrochloride (idarubicin) is separated.

g) The solution of idarubicin hydrochloride is evaporated to 50% of its original volume and was subjected to chromatographic purification.

h) The eluate was subjected to evaporation and crystallization using hydrophilic solvents, preferably low-molecular-weight aliphatic alcohols.

i) The yield of this process is 0.6 g of 4-demethoxydaunomycin hydrochloride (idarubicin hydrochloride) of 99% purity (Confirmed by HPLC).

While embodiments of the present invention have been shown and described, various modifications may be made without departing from the scope of the present invention. The invention, therefore, should not be limited, except to the following claims, and their equivalents.

What is claimed is:

1. A process for preparing 4-R-substituted anthracyclines of formula (I)

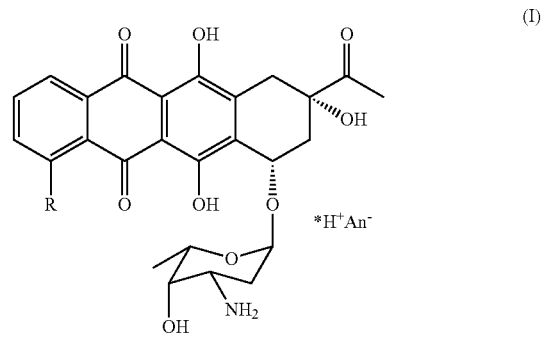

wherein R is defined as hydrogen, a linear or branched oxyalkyl, oxyalkenyl or oxyalkynyl group comprised of one to sixteen carbon atoms, or a ester group $COOR_1'$, wherein $R_1'$ is a linear or branched alkyl, alkenyl or alkyne group of up to ten carbon atoms, and An— is an anion, comprising the steps of:

(1) providing 4-demethyldaunorubicin or a derivative of 4-demethyldaunorubicin of formula (II)

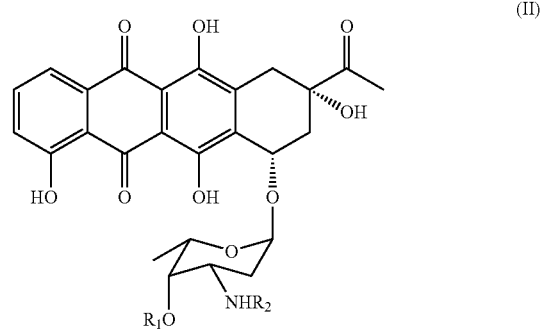

wherein $R_1$ comprises H, acyl or acyl halide and $R_2$ comprises H, acyl or acyl halide, carbonate, or Schiff's base;

(2) treating the 4-demethyldaunorubicin or the derivative of 4-demethyldaunorubicin of formula (II) with a sulfonylating agent having a chemical formula $R_3$—$SO_2$—X, wherein $R_3$ comprises an acyl group, acyl halide group or aryl group, X comprises a halide or —O—$SO_2$—$R_3$ to form 4-demethyl-4-sulfonyldaunorubicin having formula (III)

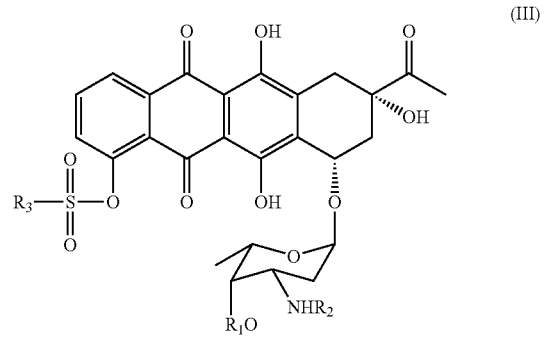

wherein $R_3$ comprises an alkyl group, alkyl halide group or an aryl group, $R_1$ comprises hydrogen, acyl, or acyl halide, and $R_2$ comprises hydrogen, acyl, acyl halide, carbonate, or Schiff's base;

(3) reacting the 4-demethyl-4-sulfonyl-daunorubicin of formula (III) with a reducing agent in the presence of catalytic quantities of a compound having formula (N)

     (IV)

wherein M represent a transition metal atom; and wherein L and L' represent the same or different anions or a neutral molecule, and p and q may vary from zero to four, to produce protected 4-demethoxydaunomycin having a formula (V),

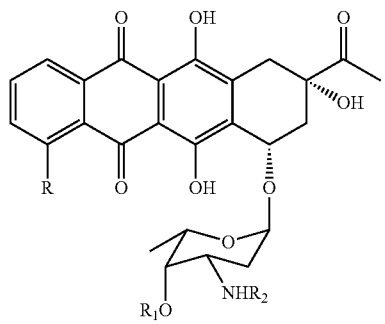

(4) hydrolyzing the protected 4-demethoxydaunomycin in a basic solution to produce 4-R-substituted anthracyclines of formula (I).

2. The process of claim 1, wherein transition metal M comprises palladium.

3. The process of claim 1, wherein transition metal M comprises nickel.

4. The process of claim 1, wherein L comprises an anion neutral molecule selected from the group consisting of HCOO⁻, CH3COO⁻, Cl⁻, a neutral solvent molecule, monophosphine, diphosphine, phosphate, and diamine.

5. The process of claim 4, wherein L comprises a chelating diphosphine selected from the group consisting of 1,3-diphenylphosphinopropane, 1,1'-bis(diphenylphosphino)ferrocene, and 1,2-bis[N-(1-phenylethyl),N-(diphenylphosphino)amino]ethane.

6. The process of claim 1, wherein L' comprises an anion neutral molecule selected from the group consisting of HCOO⁻, CH3COO⁻, Cl⁻, a neutral solvent molecule, monophosphine, diphosphine, phosphate, and diamine.

7. The process of claim 6, wherein L' comprises a chelating diphosphine selected from the group consisting of 1,3-diphenylphosphinopropane, 1,1'-bis(diphenylphosphino)ferrocene, and 1,2-bis[N-(1-phenylethyl),N-(diphenylphosphino)amino]ethane.

8. The process of claim 1, wherein the reducing agent comprises formic acid or salts of formic acid.

9. The process of claim 1, wherein R in formula (I) comprises a linear or branched oxyalkyl, oxyalkenyl or oxyalkynyl group comprised of one to sixteen carbon atoms.

10. The process of claim 9, wherein R in formula (I) comprises a linear or branched oxyalkyl, oxyalkenyl or oxyalkynyl group comprised of one to sixteen carbon atoms partially substituted by a group selected from the groups consisting of an aryl group, an alkoxy group, a trialkysilyl group, an ester group, and an amide group.

11. The process of claim 1, wherein R comprises a ester group COOR$_1$', wherein R$_1$' is a linear or branched alkyl, alkenyl or alkyne group of up to ten carbon atoms.

12. A process for preparing idarubicin of formula (I)

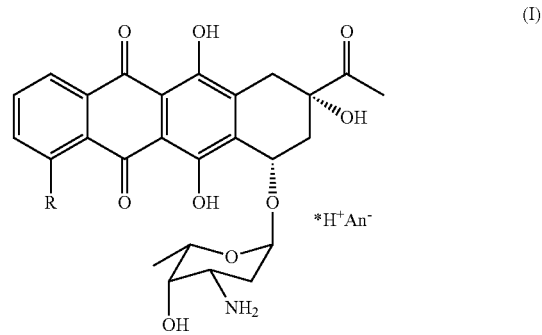

wherein R is H and An$^{31}$ comprises an anion of an acid, comprising the steps of:

(1) providing 4-demethyldaunorubicin or a derivative of 4-demethyldaunorubicin of formula (II)

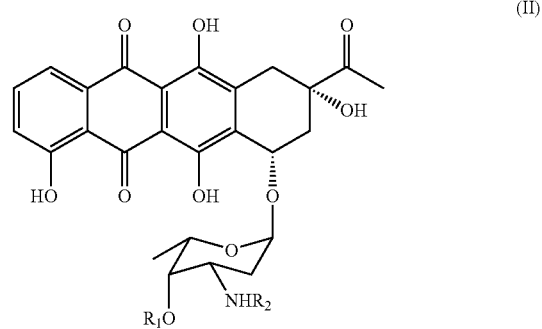

wherein $R_1$ comprises H and $R_2$ comprises trifluoroacetyl, (2) treating the 4-demethyldaunorubicin or the derivative of 4-demethyldaunorubicin of formula (II) with a sulfonylating agent comprising trifluoromethanesulfonic anhydride to form 4-trifluoromethanesulfonyl-3'-trifluoroacetamido-4-demethyldaunorubicin, (3) reacting the 4-trifluoromethanesulfonyl-3'-trifluoroacetamido-4-demethyldaunorubicin with a reducing agent in the presence of catalytic quantities of palladium acetate to produce 4-demethoxy-3'-trifluoroacetamidodaunomycin, and (4) hydrolyzing the 4-demethoxy-3'-trifluoroacetamidodaunomycin in a basic solution to produce idarubicin of formula (1).

13. The process of claim 12, wherein idarubicin of formula (I) comprises idarubicin hydrochloride.

* * * * *